(12) United States Patent
Caliendo et al.

(10) Patent No.: US 12,338,266 B2
(45) Date of Patent: Jun. 24, 2025

(54) MONTELUKAST ESTERS AND PHARMACEUTICAL COMPOSITIONS CONTAINING THE SAME

(71) Applicant: GENETIC S.P.A., Castel San Giorgio (IT)

(72) Inventors: Giuseppe Caliendo, Marigliano (IT); Giuseppe Cirino, Naples (IT); Ferdinando Fiorino, Benevento (IT); Francesco Frecentese, Aversa (IT); Marcelo Nicolas Muscara', Campinas (BR); Elisa Perissutti, Venafro (IT); Antonio Petti, Battipaglia (IT); Vincenzo Santagada, Naples (IT); Beatrice Severino, Mugnano di Napoli (IT); Fiorentina Roviezzo, Bonea (IT)

(73) Assignee: GENETIC S.P.A., Castel San Giorgio SA (IT)

( * ) Notice: Subject to any disclaimer, the term of this patent is extended or adjusted under 35 U.S.C. 154(b) by 758 days.

(21) Appl. No.: 17/629,914

(22) PCT Filed: Aug. 4, 2020

(86) PCT No.: PCT/EP2020/071930
§ 371 (c)(1),
(2) Date: Jan. 25, 2022

(87) PCT Pub. No.: WO2021/023751
PCT Pub. Date: Feb. 11, 2021

(65) Prior Publication Data
US 2022/0251136 A1 Aug. 11, 2022

(30) Foreign Application Priority Data
Aug. 6, 2019 (IT) .................. 102019000014178

(51) Int. Cl.
*A61K 31/58* (2006.01)
*A61P 11/00* (2006.01)
*A61P 11/06* (2006.01)
*C07J 71/00* (2006.01)

(52) U.S. Cl.
CPC .................. *C07J 71/0031* (2013.01)

(58) Field of Classification Search
CPC ...... C07J 71/0031; A61K 31/58; A61P 11/00; A61P 11/06
See application file for complete search history.

(56) References Cited

FOREIGN PATENT DOCUMENTS

| WO | WO2006138232 | 12/2006 |
|---|---|---|
| WO | WO2009052624 | 4/2009 |
| WO | WO2010126953 | 11/2010 |
| WO | WO2010132743 | 11/2010 |

OTHER PUBLICATIONS

Derom, Eric, et al., "Effects of inhaled ciclesonide and fluticasone propionate on cortisol secretion and airway responsiveness to adenosine 5' monophosphate in asthmatic patients", Pulmonary Pharmacology & Therapeutics, ,18, 2004, pp. 328-336.
Dos Santos, Pedro, et al., "Modified in vivo lung perfusion allows for prolonged perfusion without actue lung injury", The Journal of Thoracic and Cardiovascular Surgery, vol. 147, No. 2, Feb. 2014, pp. 774-782.
Eum, Seok-Yong, et al., "Involvement of the Cysteinyl Leukotrienes in Allergen Induced Airway Eosinophilis and hyperresponsiveness in the Mouse", Am. J. Respir. Cell Nol. Siol., vol. 28, 2003, pp. 25-32.
Foster, Juliet M., et al., "Higher patient perceived side effects related to higher daily doses of inhaled corticosteroids in the community: a cross-sectional analysis", Respiratory Medicine, 300, 2006, pp. 1318-1336.
Handbook of Pharmaceutical Salts, edited by Stahl, P. Henrich, et al., 2008 pp. 127-133.
Henderson, William R., Jr., et al., "A Role for Cysteinyl Leukotrienes in Airway Remodeling in a Mouse Asthma Model", Am J Respir Crit Care Med, Bol. 165, 2002, pp. 108-116.
International Search Report for PCT/EP2020/0719380 dated Oct. 20, 2020.
Kim, Hwan Soo, et al., "Effect of Proparacaine in a Mouse Model of Allergic Rhinitis", Clinical and Experimental Otorhinolaryngology, vol. 10, No. 3, Dec. 2017, pp. 325-331.
Laforest, Laurent, et al., "Asthma patients self-reported behaviours toward inhaled corticosteroids", Respiratory Medicine, 103, 2009, pp. 1366-1375.
Wu, A. Y., et al., "Anti-inflammatory effects of high-dose montelukast in an animal model of acute asthma", Clin. Exp Allergy, 33, 2003, pp. 359-366.
Zuska-Prot, Monika, et al., "Effect of inhaled and systemic glucocorticoid treatment on CD4+ regulatory and effector T cells in a mouse model of allergic asthma", International Immunopharmacology, 45, 2017, pp. 98-109.
Zuska-Prot, Monika, et al., "Inhaled glucocorticoid treatment prevents the response of CD8+ T cells in a mouse model of allergic asthma and causes their depletion outside the respiratory system", International Immunopharmacology, 53, 2017, pp. 63-72.

*Primary Examiner* — Brenda L Coleman
(74) *Attorney, Agent, or Firm* — HUESCHEN AND SAGE (57) ABSTRACT

The present invention relates to esters of Montelukast with corticosteroids, preferably with des-ciclesonide, triamcinolone, budesonide or flunisolide, pharmaceutical compositions containing the same and the use thereof in the treatment of several respiratory tract diseases, especially asthma, chronic obstructive pulmonary disease (COPD) and allergic rhinitis. The invention further relates to the process for preparing said esters.

16 Claims, 11 Drawing Sheets

MONTELUKAST ESTERS AND PHARMACEUTICAL COMPOSITIONS CONTAINING THE SAME

The present invention relates to esters of Montelukast with corticosteroids, preferably with des-ciclesonide, triamcinolone, budesonide or flunisolide, pharmaceutical compositions containing the same and the use thereof in the treatment of several respiratory tract diseases, especially asthma, chronic obstructive pulmonary disease (COPD) and allergic rhinitis. The invention further relates to the process for preparing said esters.

BACKGROUND OF THE INVENTION

Inhaled corticosteroids (ICS) are still the mainstay of treatment in asthma. The most important factor when deciding on ICS treatment is the ratio between risk/benefit of the selected ICS. Research over the past decades has shown that not all the patients have equal response. Indeed, while some patients might experience very few side effects from even high-dose ICS, a survey based on direct interview with the patients (1) has demonstrated that several side effects such as hoarseness, thin skin and disturbed vision are under evaluated. Measurements of patient population with the inhaled corticosteroids questionnaire showed that 45% of patients reported moderate to severe side effects due to ICS when given in a dose >800 mcg daily. A study from Laforest et al (2) showed that 32% of patients who started ICS treatment subsequently stopped because of perceived side effects. To the present stage ICS discontinuation is the most common cause of lack of asthma control in mild to moderate asthma.

Ciclesonide, ((11β,16α)-16,17-[[(R)-cyclohexylmethylene]bis(oxy)]-11-hydroxy-21-(2-methyl-1-oxopropoxy)pregna-1,4-diene-3,20-dione. Formula I) is an ICS approved for the treatment of asthma and allergic rhinitis.

FORMULA I

Ciclesonide is a pro-drug that, after intranasal application, is enzymatically hydrolyzed to a pharmacologically active metabolite, C21-desisobutyryl-ciclesonide (des-ciclesonide or des-Cic, Formula I). Des-ciclesonide has anti-inflammatory activity with affinity for the glucocorticoid receptor that is 120 times higher than the parent compound. The precise mechanism through which ciclesonide affects allergic rhinitis symptoms is unknown.

FORMULA II

Ciclesonide and des-ciciesonide have negligible oral bio-availability (both less than 1%) due to low gastrointestinal absorption and high first-pass metabolism. The intranasal administration of ciclesonide at recommended doses results in negligible serum concentrations of ciclesonide.

Ciclesonide is activated only in the lung, with low oral and high pulmonary deposition, high first pass effect in the liver and high protein binding in the blood stream. Of note, cortisol suppression of ciclesonide was comparable with placebo (3). Several clinical studies have also demonstrated that patients perceive a difference in the number and intensity of side effects between ciclesonide and other ICS. More patients treated with ciclesonide (once daily) were at least satisfied with their treatment. Therefore, the dosage, inhaler type and the administration frequency, but also the choice of ICS drug is crucial in modern clinical practice. The difference might not lie not only in efficacy per microgram bust mostly in patients appreciation of the balance between efficacy and low adverse events-both local and systemic-which are relevant for clinical practice.

Montelukast sodium has the chemical name (R,E)-2-(1-((1-(3-(2-(7-chloroquinolin-2-yl)vinyl)phenyl)-3-(2-(2-hydroxypropan-2-yl)phenyl)propylthio)-methyl)cyclopropyl)acetic acid monosodium salt and is represented by Formula III. It selectively and competitively blocks the cysteinyl leukotriene CysLT1 receptor preventing binding of the inflammatory mediator leukotriene D4 (LTD4). It shows both anti-inflammatory and bronchodilator effects, and is approved for the treatment of chronic asthma.

Montelukast sodium (10 mg) orally administered once daily at bedtime demonstrated improvement in variables of asthma control, including forced expiratory volume in 1 second ($FEV_1$), daytime and night time symptom scores, and as-needed β-agonist use.

FORMULA III

Montelukast sodium is a hygroscopic, optically active, white to off-white powder, prepared from the free carboxylic acid ((R,E)-2-(1-((1-(3-(2-(7-chloroquinolin-2-yl)vinyl) phenyl)-3-(2-(2-hydroxypropan-2-yl)phenyl)propylthio)-methyl)cyclopropyl)acetic acid, Formula IV) upon treatment with a sodium ion source.

It is freely soluble in ethanol, methanol, and water and practically insoluble in acetonitrile,

FORMULA IV

Many studies have been published in the past 10 years on the efficacy and safety of montelukast in asthma. Experimental and clinical studies on a large number of patients with asthma of different severity have demonstrated that montelukast modifies the pathophysiological mechanisms of the disease and improves, to some extent, the clinical and functional manifestations of asthma. In particular clinical studies performed with montelukast in combination with other drugs, such as inhaled corticosteroids, have contributed to the clinical positioning of montelukast at different levels of asthma treatment according to the Global Initiative for Asthma Guidelines. Montelukast is often used in addition to ICS for i) improving clinical manifestations by an increase in anti-inflammatory effects and ii) to reduce corticosteroid use. The safety profile of montelukast is very good and its efficacy has been demonstrated in different clinical and biological phenotypes of asthma.

Definitions

Unless otherwise defined, all terms of art, notations and other scientific terminology used herein are intended to have the meanings commonly understood by those of skill in the art to which this disclosure pertains. In some cases, terms with commonly understood meanings are defined herein for clarity and/or for ready reference; thus, the inclusion of such definitions herein should not be construed to represent a substantial difference over what is generally understood in the art.

The term "physiologically acceptable excipient" herein refers to a substance devoid of any pharmacological effect of its own and which does not produce adverse reactions when administered to a mammal, preferably a human. Physiologically acceptable excipients are well known in the art and are disclosed, for instance in the Handbook of Pharmaceutical Excipients, sixth edition 2009, herein incorporated by reference.

The term "pharmaceutically acceptable salts thereof" herein refers to those salts which possess the biological effectiveness and properties of the salified compound and which do not produce adverse reactions when administered to a mammal, preferably a human. The pharmaceutically acceptable salts may be inorganic or organic salts, examples of pharmaceutically acceptable salts include but are not limited to: carbonate, hydrochloride, hydrobromide, sulphate, hydrogen sulphate, citrate, maleate, fumarate, trifluoroacetate, 2-naphthalenesulphonate, and par-toluenesulphonate. Further information on pharmaceutically acceptable salts can be found in Handbook of pharmaceutical salts, P. Stahl, C. Wermuth, WILEY-VCH, 127-133, 2008, herein incorporated by reference.

The term "Montelukast" herein refers to Montelukast free carboxylic acid.

The term "corticosteroids" herein refer to Inhaled corticosteroids (ICS) such as des-ciclesonide, triamcinolone, budesonide and flunisolide, preferably des-ciclesonide.

The term "pediatric population" herein refers to that part of the population from birth to eighteen years.

The term "isomers" refers to structural (or constitutional) isomers, i.e. tautomers and stereoisomers (or spatial isomers), i.e. diastereoisomers and enantiomers.

The term "prodrugs" refers to pharmacologically inactive derivatives that may undergo in vivo metabolic transformation to provide an active compound.

The terms "approximately" and "about" herein refer to the range of the experimental error, which may occur in a measurement.

The terms "comprising", "having", "including" and "containing" are to be construed open-ended terms (i.e, meaning "including, but not limited to") and are to be considered as providing support also for terms as "consist essentially of", "consisting essentially of", "consist of" or "consisting of".

The terms "consist essentially of", "consisting essentially of" are to be construed as semi-closed terms, meaning that no other ingredients which materially affects the basic and novel characteristics of the invention are included (optional excipients may thus included).

The terms "consists of", "consisting of" are to be construed as closed terms.

SUMMARY OF THE INVENTION

Several studies have shown that combination therapy using inhaled corticosteroids (ICS) associated to bronchodilators confers complementary and synergistic effect in the management of asthma. For this reason a wide number of combinations have been explored and marketed.

Montelukast sodium is prescribed as monotherapy or in combination with other asthma medications, including ICS, for the treatment of asthma. Several studies have shown that for patients whose asthma is not controlled with ICS therapy, adding a second drug rather than increasing the dose of ICS results in improved control of symptoms.

The aim of the present invention is to provide novel Montelukast esters having a synergistic therapeutic effect.

According to a first aspect, the present invention relates to the esters of Montelukast with corticosteroids, preferably the corticosteroid is selected from the group of Inhaled corticosteroids (ICS) comprising des-ciclesonide, triamcinolone, budesonide and flunisolide.

A second aspect of the present invention is a process for the preparation of the above Montelukast esters.

A third aspect of the present invention are pharmaceutical compositions comprising said Montelukast esters in combination with at least one physiologically acceptable excipient.

A fourth aspect of the present invention are the above Montelukast esters and pharmaceutical compositions for use as medicaments.

A fifth aspect of the present invention are the above Montelukast esters and pharmaceutical compositions for use in treating several respiratory tract diseases, preferably asthma, chronic obstructive pulmonary disease (COPD) and allergic rhinitis.

DESCRIPTION OF THE FIGURES

FIG. 8. Effects of Montelukast desisobutyryl-ciclesonide ester (MC) and ciclesonide (Ciclo) on Penh measurements in mice with OVA-induced allergic asthma. Bronchoconstriction was assessed by the enhanced pause response (Penh) measured after exposure of the unrestrained animals to Inhaled saline solution (panel B) and increasing concentrations of inhalatory methacholine (MCh; panel A). Montelukast desisobutyryl-ciclesonide ester or ciclesonide were administered daily for 4 weeks, and 30 min before the OVA challenge (twice a week). Each data point represents mean±SEM for n=6 animals/group, except for Sham group (n=5). Panel A: MCh dose vs. response curves; panel C: peak Penh responses (Emax); panel D: areas under the Penh vs. MCh dose curves (AUC). *P<0.05 and **P<0.01 vs. Sham: #P<0.05 and ##P<0.01 vs. untreated OVA group, as analyzed by one-way ANOVA followed by the Dunnett test.

DETAILED DESCRIPTION OF THE INVENTION

The present invention relates to an ester of Montelukast with a corticosteroid.

In a preferred embodiment of the invention, the corticosteroid is selected from the group of inhaled corticosteroids (ICS) comprising des-ciclesonide, triamcinolone, budesonide and flunisolide.

More preferably, the present invention relates to a montelukast desisobutyryl-ciclesonide ester of Formula V:

FORMULA V or a pharmaceutically acceptable salt, biologically active metabolite, solvate, hydrate, prodrug, isomer thereof.

The 21-OH group of des-ciclesonide has been reacted with the —COOH group of montelukast, affording an ester that combines the high efficacy and long tasting action of ciclesonide with the decreasing number of times to use the rescue inhaler provided by montelukast. The montelukast desisobutyryl-ciclesonide ester (Formula V), differently from montelukast sodium salt that cannot be administered intranasally, and in analogy with ciclesonide that works as a prodrug, can be inhaled because of its higher hydrophobicity.

The esters of the present invention allow to improve patient convenience and compliance through unifying a multi-faceted treatment into a single dose of drug.

As will be shown in the experimental section, montelukast desisobutyryl-ciclesonide ester significantly reduces allergen-induced airway dysfunction.

In addition, the ester of the present invention significantly reduces allergen-induced IgE raise, implying the ability to prevent exacerbation episodes in asthma management.

Moreover, the data obtained demonstrate the synergistic effect of the ester MC with respect to montelukast and ciclesonide administered alone.

Another aspect of this invention relates to a pharmaceutical composition comprising as active ingredient a Montelukast ester with a corticosteroid in combination with at least one physiologically acceptable excipient.

Preferably, said compositions are in the form of aerosol, dry powder, solution or suspension, more preferably said compositions are administered by inhalation or oral route.

For the administration by inhalation, the compound of the invention may be suitably inhaled from a nebulizer, from a pressurized metered dose inhaler or as a dry powder from a dry powder inhaler (e.g. Turbuhaler®) or from a dry powder inhaler utilizing gelatine, plastic or other capsules, cartridges or blister packs.

The pharmaceutical compositions suitable for oral use can be administered in the form of tablets, capsules or syrups.

Another aspect of the invention relates to the Montelukast esters or their pharmaceutical compositions according to the invention for use as a medicament.

According to a preferred embodiment of the invention, the Montelukast esters or their pharmaceutical compositions are useful in treating several respiratory tract diseases, especially asthma, chronic obstructive pulmonary disease (COPD) and allergic rhinitis.

The Montelukast esters or their pharmaceutical compositions according to the invention are useful in adult or pediatric population.

Another aspect of the invention relates to a process for the preparation of the Montelukast esters according to the invention, comprising the steps of:
i) dissolving or suspending Montelukast and a corticosteroid in an organic solvent;
ii) isolating the ester of Montelukast with the corticosteroid.

In a preferred embodiment of the invention, the corticosteroid is selected from the group of Inhaled corticosteroids (ICS) comprising des-ciclesonide, triamcinolone, budesonide and flunisolide.

Preferably, the isolated ester of Montelukast is montelukast desisobutyryl-ciclesonide ester.

The useful organic solvents include C1-C4 chlorinated hydrocarbons (dichloromethane, chloroform, dichloroethane), C2-C4 nitriles (acetonitrile) and N,N-dimethyl-amides (DMF, DMA) or mixtures thereof.

Preferably, said organic solvent is selected from the group consisting of C1-C4 chlorinated hydrocarbons (dichloromethane, chloroform, dichloroethane) and N,N-dimethyl-amides or mixtures thereof. More preferably, said solvent is selected from the group consisting of N,N-dimethyl-amides (DMF, DMA).

Preferably, in the process according to the invention the mmol/mL ratio between Montelukast and the organic solvent is from 0.05 mmol/mL to 0.1 mmol/mL.

Preferably, in the process according to the invention the molar ratio between Montelukast and the corticosteroid is from 1 to 1.25.

According to a preferred embodiment of the process of the invention, the isolation step ii) is carried out by crystallization, preferably from hexane, petroleum ether, diethyl ether or dichloromethane.

EXPERIMENTAL SECTION

Chemistry

1. Materials and Methods

Montelukast and ciclesonide were purchased from Carbosynth Ltd (Compton Berkshire, UK). Desisobutyryl-ciclesonide (des-CIC) was prepared as described by Phull et al. (Processes for the preparation of ciclesonide and its crystal modification. WO 2008/035066). All the other commercial products have been purchased from Merck-Sigma Aldrich. Melting points, determined using a Buchi Melting Point B-540 instrument, are uncorrected and represent values obtained on recrystallized or chromatographically purified material. NMR spectra were recorded on Varian Mercury Plus instrument at 700 MHz (for $^1$H NMR) and 400 MHz (for $^{13}$C NMR). All spectra were recorded in CDCl$_3$. Chemical shifts are reported in ppm. Fourier transform Infrared spectrum (FT-IR) was collected on a Jasco FT/IR 4100spectrometer (Easton, Md.).

FIGS. 1-4 show HRMS, $^1$H NMR, $^{13}$C NMR and FT-IR spectrum of montelukast desisobutyryl-ciclesonide ester.

2. Detailed Description of Montelukast Desisobutyryl-Ciclesonide Ester Synthesis (Formula V)

Montelukast (500 mg, 0.85 mmol), des-Cic (440 mg, 0.935 mmol), HATU (324 mg, 0.85 mmol) were dissolved in anhydrous DMF (10 mL). To the obtained solution, DIPEA (185 µL, 1.06 mmol) was added. The reaction was protected from light and monitored by TLC using dichloromethane/methanol (9.5/0.5) as eluent. After 24 h at room temperature, the reaction was quenched with water and extracted with dichloromethane. The organic phase, protected from light, was dried and concentrated. The obtained residue was purified on silica gel column using dichloromethane/methanol (9.5/0.5) as eluent. The combined fractions were concentrated and the obtained residue was crystallized from hexane affording 260 mg of pure product (yield 30%) as a white solid. HRMS calc for $C_{63}H_{72}ClNO_8S$ (M+H)$^+$ 1038.76568, exper 1038.47449. M.p. 147.0±2.1

$^1$H NMR (700 MHz, CDCl$_3$) δ 7.79-7.12 (m, 16H), 6.26 (d, 1H, desCic), 6.01 (s, 1H_desCic), 5.30 (s, 1H_DesCic), 4.82 (d, 1H_DesCic), 4.74 (s, 1H_DesCic), 4.39 (m, 1H_DesCic), 4.33 (d, 1H_DesCic), 4.11-3.96 (m, 1H_Monte), 3.18 (m, 1H_Monte), 2.94 (m, 1H_Monte), 2.60-1.67 (m, 20H), 1.62 (s, 6H, 2CH$_3$_Monte), 1.41 (s, 3H, CH$_3$_desCic), 1.20-1.02 (m, 8H), 0.89 (s, 3H, CH$_3$_desCic), 0.44-0.59 (m, 4H, CH$_3$_Monte).

$^{13}$C NMR (400 MHz, CDCl$_3$) δ 203.43, 186.57, 171.80, 169.85, 156.19, 145.22, 144.12, 140.46, 140.21, 137.64, 135.96, 131.48, 129.15, 128.99, 128.80, 127.80, 127.08, 126.26, 125.61, 125.57, 125.42, 122.47, 119.31, 107.41, 97.33, 81.74, 73.72, 69.60, 67.38, 60.36, 55.18, 50.66, 49.72, 46.00, 44.03, 40.63, 40.55, 39.93, 39.79, 39.39, 34.02, 33.37, 32.38, 31.88, 31.79, 30.89, 30.34, 27.18, 27.02, 26.21, 25.53, 21.03, 17.09, 16.96, 14.17, 12.81, 12.46.

$v_{max}$ 3422, 2930, 2853, 1727, 1859, 1608, 1497, 1442, 1408, 1370, 1240, 1148, 1058, 1016, 888, 762, 698 cm$^{-1}$.

Pharmacology

Protocol-1

Balb/c mice (8-9 weeks old, Charles River, Calco, Italy) were housed in the animal care facility at the Department of Pharmacy of the University of Naples. Italy in a controlled environment (temperature 21±2° C. and humidity 60±10%) and provided with standard rodent chow and water. All animals were allowed to acclimate for four days prior to experiments and were subjected to 12 h light-12 h dark schedule. Each mouse was assigned an identity number and randomtzed to different groups so that all experiments were carried out in a blinded manner. The experimental procedures were approved by the Italian Ministry according to International and National law and policies (EU Directive 2010/63/EU and Italian DL 26/2014 for animal experiments, ARRIVE guidelines and the Basel declaration including the 3R concept). Animal studies are reported in compliance with the ARRIVE guidelines. Balb/c mice is the most widely mouse strain used to study asthma-like features in vivo and to investigate the undedying molecular and cellular mechanisms of allergen sensitization. Mice were treated subcutaneously (s.c.) with 0.4 mL (100 µg) of ovalbumin (OVA) complexed with alum (13 mg mL$^{-1}$) (OVA group) at day 0 and 7. Chicken egg-white ovalbumin (OVA: grade V. cat. A5503, Sigma Chemical Co., St. Louis, MO) was dissolved in sterile phosphate buffered saline (PBS) solution (250 µg/1 ml) and Al(OH)$_3$ was added (at 13 mg/ml). This mix was used to induce the allergic sensitization of the animals by subcutaneous injection. OVA was dissolved at 3% in sterile PBS solution and this solution was nebulized (as the immunological challenges). At day 21 mice were exposed to OVA challenge for three days and then sacrificed. This experimental procedure induces in the mice an increase in plasma IgE levels and this effect is by itself sufficient to induce a significant increase in bronchial hyper-responsiveness and pulmonary inflammation, typical hallmarks of asthma. A group of animals was treated s.c. with saline (vehicle group). The sensitized mice were treated intraperitoneally (i.p.) with montelukast desisobutyryl-ciclesonide ester (0.5, 1 and 2 mg/Kg) 1 hour before OVA challenge. In another set of experiments sensitized mice were treated intraperitoneally (i.p.) with Montelukast (1 mg/kg) or cicloesonide (1 mg/kg) 1 hour before each OVA injection. Animals were killed at selected time points by overdose of enflurane and bronchi and blood collected.

Protocol-2

Male Balb/c SPF mice (26*2 g, 6 week-old) were purchased from the animal house facilities at the Faculty of Medicine (University of São Paulo, Brazil). They were group-housed in a temperature-controlled room at 22° C. with a 12/12-hour light/dark cycle and allowed free access to food and water. The study is in agreement with the Ethical Principles for Animal Research established by the Brazilian College for Animal Experimentation (COBEA). According to the internal laboratory rules, euthanasia will be performed if severe distress related to the test agents developed during the experiment. Mice were sensitized with two subcutaneous injections of 0.2 ml of OVA/Al(OH)$_3$, with an interval of 7 days (Sham animals received the Al(OH)$_3$ suspension in PBS with no OVA). Chicken egg-white ovalbumin (OVA; grade V, cat. A5503, Sigma Chemical Co., St. Louis, Mo.) was dissolved in sterile phosphate buffered saline (PBS) solution (50 µg/ml) and Al(OH)$_3$ was added (at 8 mg/ml). This mix was used to induce the allergic sensitization of the animals by subcutaneous injection. OVA was dissolved at 1% in sterile PBS solution and this solution was nebulized (as the immunological challenges). Seven days after the second sensitization (i.e., 3$^{rd}$ week), the animals were nebulized twice a week with the 1% OVA solution (Sham and untreated OVA groups were nebulized with PBS) during 20 minutes for the next 4 weeks. Thirty minutes before the challenges (OVA nebulization) and daily during the next 4 weeks, mice were intra-nasally treated (10 µl/animal as 5 µl/nostril) with the respective compounds/vehicle. The sensitized mice were treated intranasally (i.n.) with montelukast desisobutyryl-ciclesonide ester (10, 30 and 100 nmol/animal) 30 min before OVA challenge. In another set of experiments sensitized mice were treated i.n. with Montelukast (10 nmol/animal) or cicloesonide (100 nmol/animal) 30 min before each OVA injection. Animals were killed at selected time points by overdose of enflurane and BAL and blood collected.

Measurement of Bronchial Reactivity

Main bronchi were rapidly dissected and cleaned from fat and connective tissue. Rings of 1-2 mm length were cut and mounted in 2.5 mL isolated organ baths containing Krebs solution, at 37° C., oxygenated (95% O$_2$ and 5% CO$_2$), and connected to an isometric force transducer (type 7000. Ugo Basile. Cornerio, Italy) associated to a Powerlab 800 (AD Instruments). Rings were initially stretched until a resting tension of 0.5 g and allowed to equilibrate for at least 30 min. In each experiment bronchial rings were previously challenged with acetylcholine (10$^{-6}$ M) until a reproducible response curve was obtained. Subsequently, after tissue washing, a cumulative concentration response curve to carbachol (10$^{-9}$-3×10$^{-6}$ M) was performed. Results were expressed as dyne/mg tissue. In another set of experiments on bronchi pre-contracted with carbachol and salbutamol-induced relaxation was assessed.

Measurement of Plasma IgE Levels

Blood was collected by intracardiac puncture using citrate as anticoagulant. Plasma was obtained by centrifugation at 800×g at 4'C for 10 minutes and immediately frozen at −80° C. Total IgE levels were measured by means of ELISA using matched antibody pairs (BD Biosciences Pharmingen San Jose, Calif.).

Lung Hyperreactivity/Penh Function

Airway responsiveness in conscious, spontaneously breathing animals was measured at the end of the 6$^{th}$ week (i.e., after 4 weeks OVA challenges+treatments), 24 h after the last OVA/PBS challenge via whole body plethysmography (Buxco Europe Ltd, Winchester, UK). Experiments were carried out in a quiet room by an investigator who was unaware of the nature of treatments. Aerosolized saline (50 µl/mouse during 60 s) and then the muscarinic agonist metacholine (MCh) at increasing concentrations (3.12, 6.25, 12.5 and 25.0 mg/ml in PBS) was nebulized through an inlet of the main chamber for 3 min each to induce bronchoconstriction and readings were taken and averaged for 6 min following each nebulization. After 20 min. the baseline values usually returned at the end of this period. Enhanced pause (Penh) was measured as an indicator of bronchoconstriction and consequent increase of airway resistance as: Penh=[(expiration time/relaxation time)−1]/(maximum expiration flow/maximum inspiration flow).

Collection of BAL Fluid and Blood Samples

After Penh evaluation, the mice were anesthetized with inhaled isofluorane (5% v/v in $O_2$) and blood samples were collected from the descending abdominal aorta. The mice were then euthanized by exsanguination and bronchoalveolar lavage (BAL) was performed by exposing and cannulating the trachea with a polyethylene tube (1 mm outer diameter) connected to a syringe. The lungs were washed by flushing 300 μL of heparin-containing PBS solution (20 UI/mL). The retrieved BAL lavage aliquots were obtained and the same procedure was repeated four additional times. The samples were centrifuged (1000 g for 10 min) and the cell pellet was resuspended in 200 μL of PBS solution, Total cell counts were determined using a Neubauer chamber, and differential counting was carried out in cytospin (Fanem Mod 2400; São Paulo, Brazil) preparations stained with May-Grünwald dye. Leukocytes were classified based on morphological criteria.

Statistical Analysis

The results are expressed as mean±S.E.M of the mean of n observations, where n represents the number of animals, Statistical evaluation was performed by one-way or two-way ANOVA using GraphPad InStat (Graphpad Software Inc., San Diego, Calif.) followed by a Bonferroni post-hoc test for multiple comparisons, respectively. Post hoc tests were run only when F achieved $P<0.05$ and there was no significant variance in homogeneity. A P value $<0.05$ was used to define statistically significant differences between mean values.

Protocol 1: Results

Figure 1:
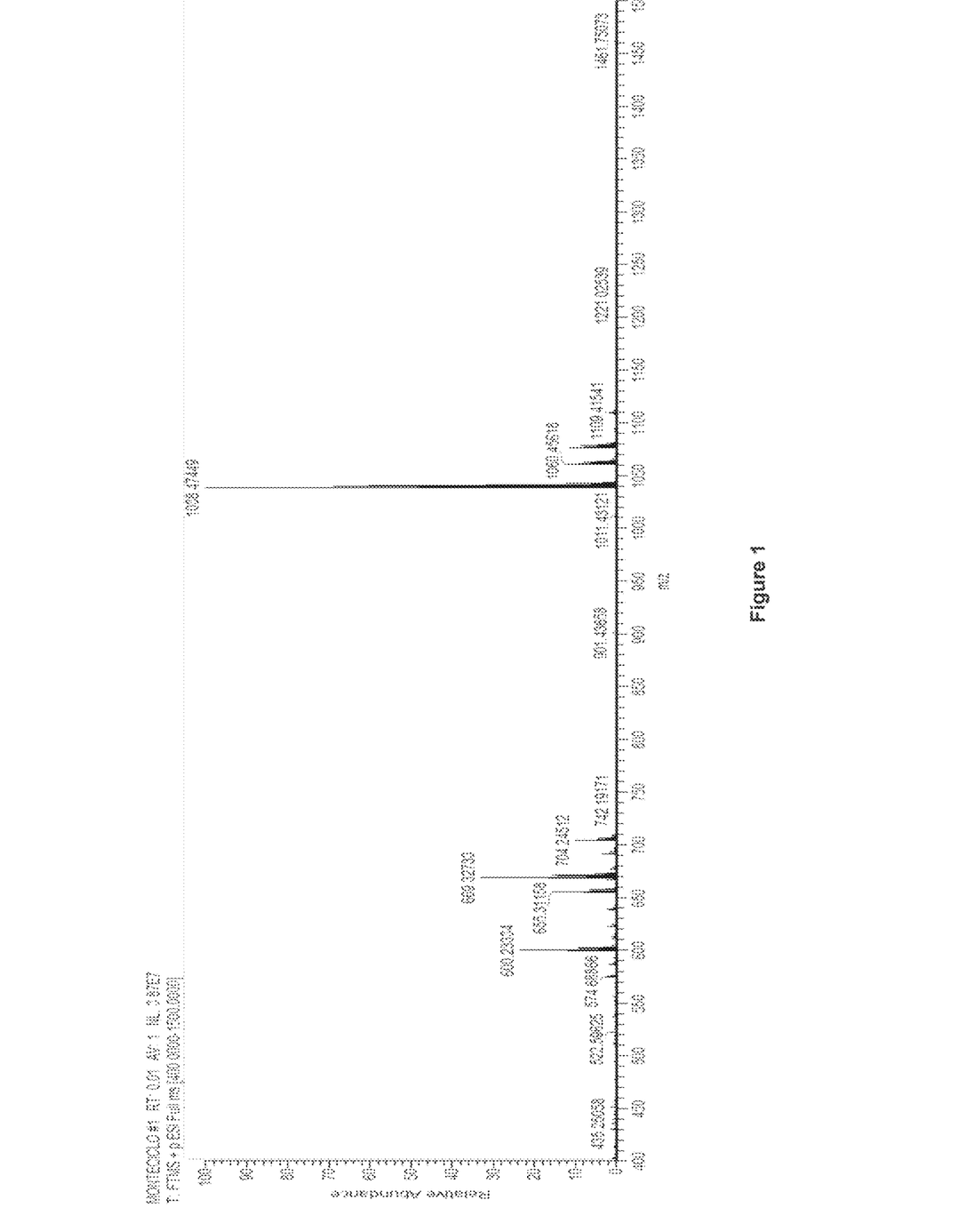
FIG. 1. HRMS of montelukast desisobutyryl-ciclesonide ester.
Figure 2:
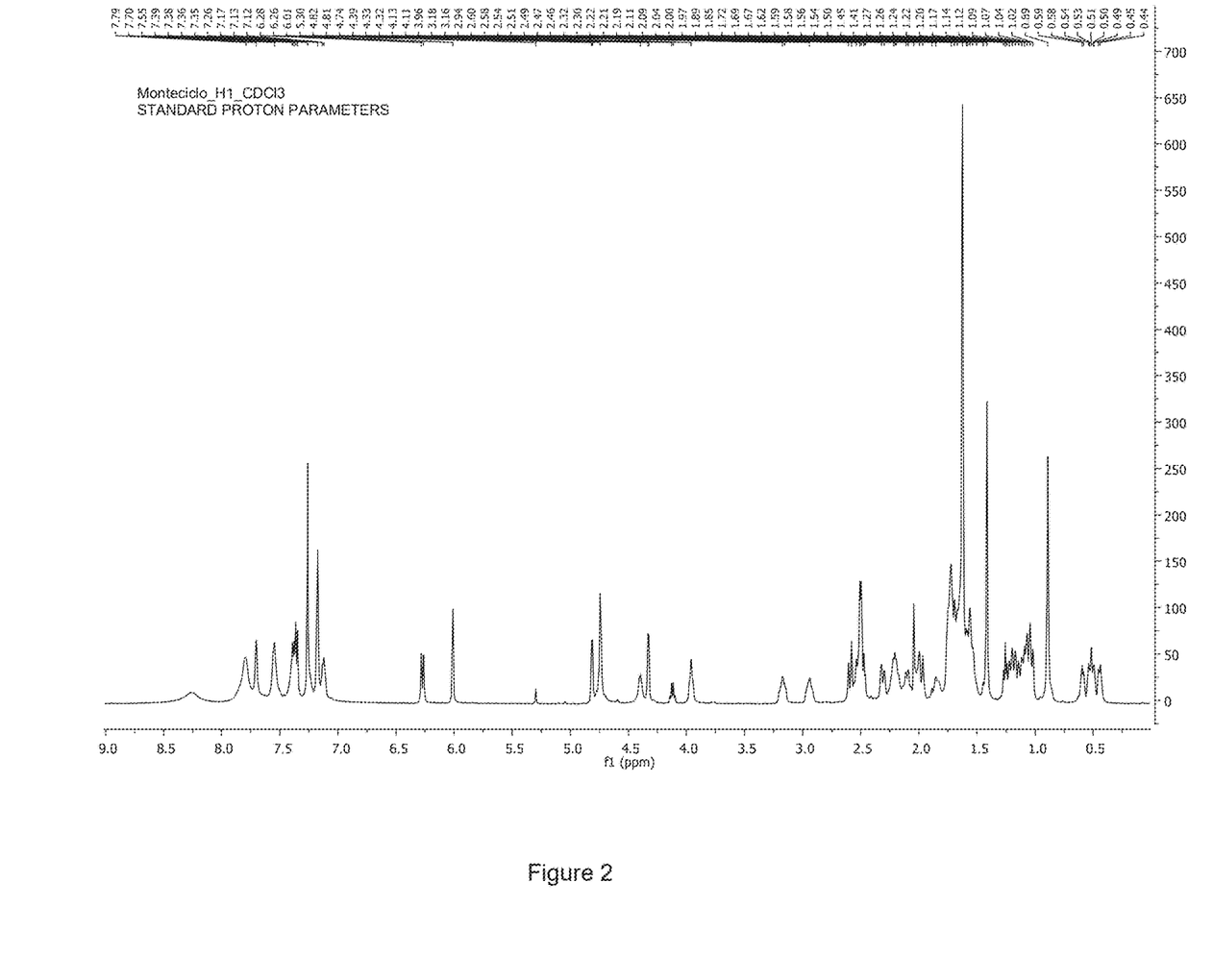
FIG. 2. $^1$H NMR of montelukast desisobutyryl-ciclesonide ester in CDCl$_3$ (700 MHz).
Figure 3:
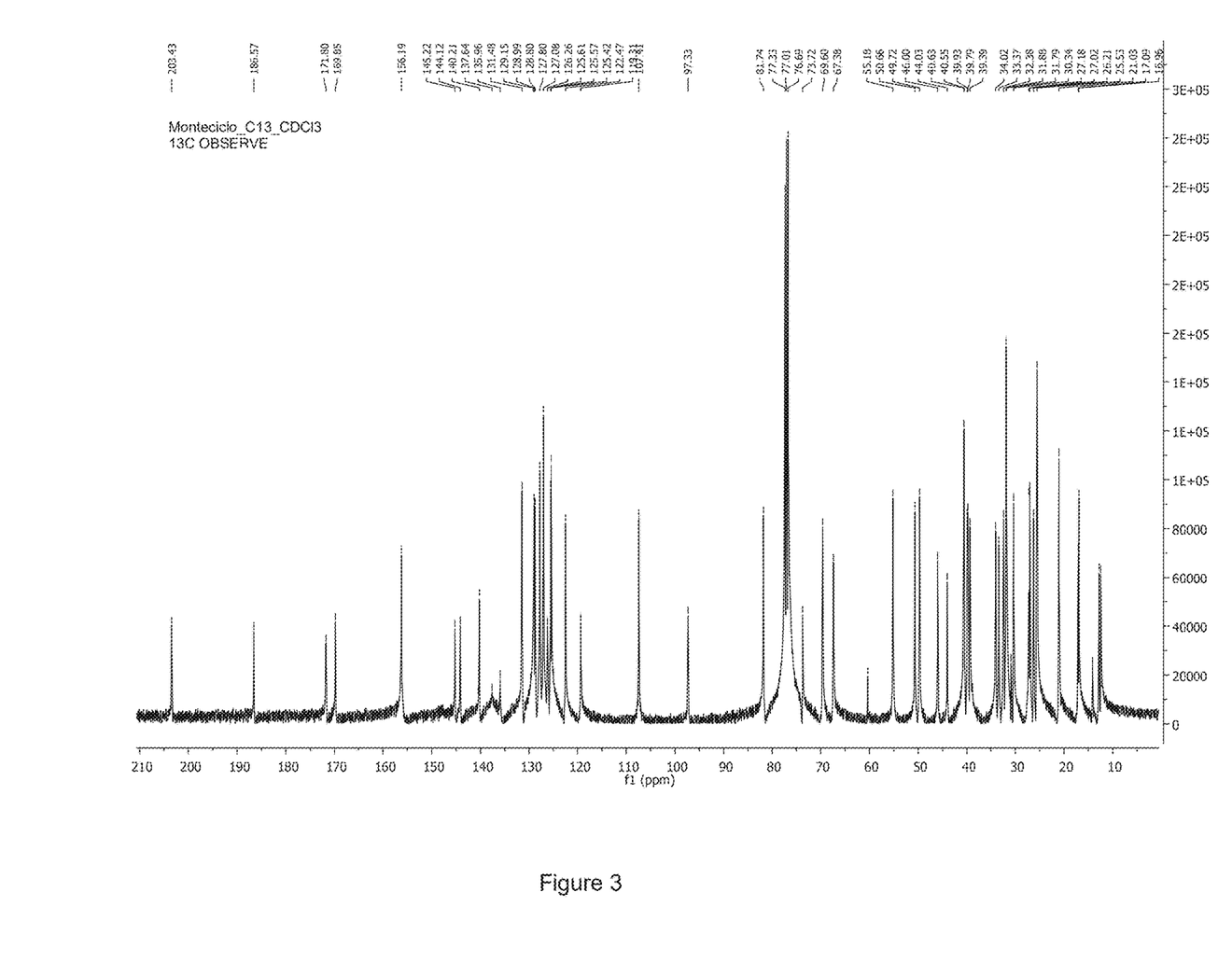
FIG. 3. $^{13}$C NMR of montelukast desisobutyryl-ciclesonide ester in CDCl$_3$ (400 MHz).
Figure 4:
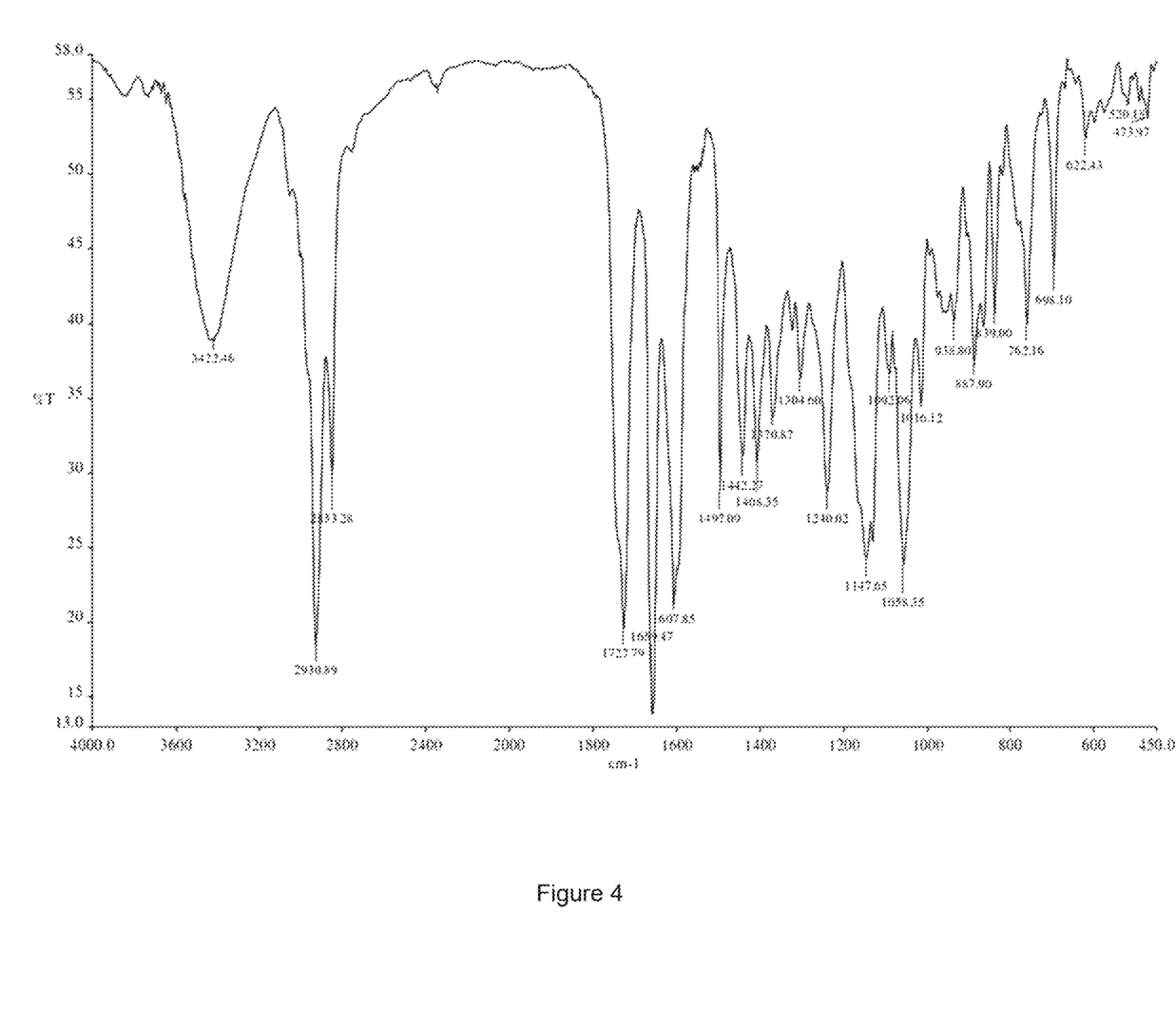
FIG. 4. FT-IR spectrum of montelukast desisobutyryl-ciclesonide ester.
Figure 5:
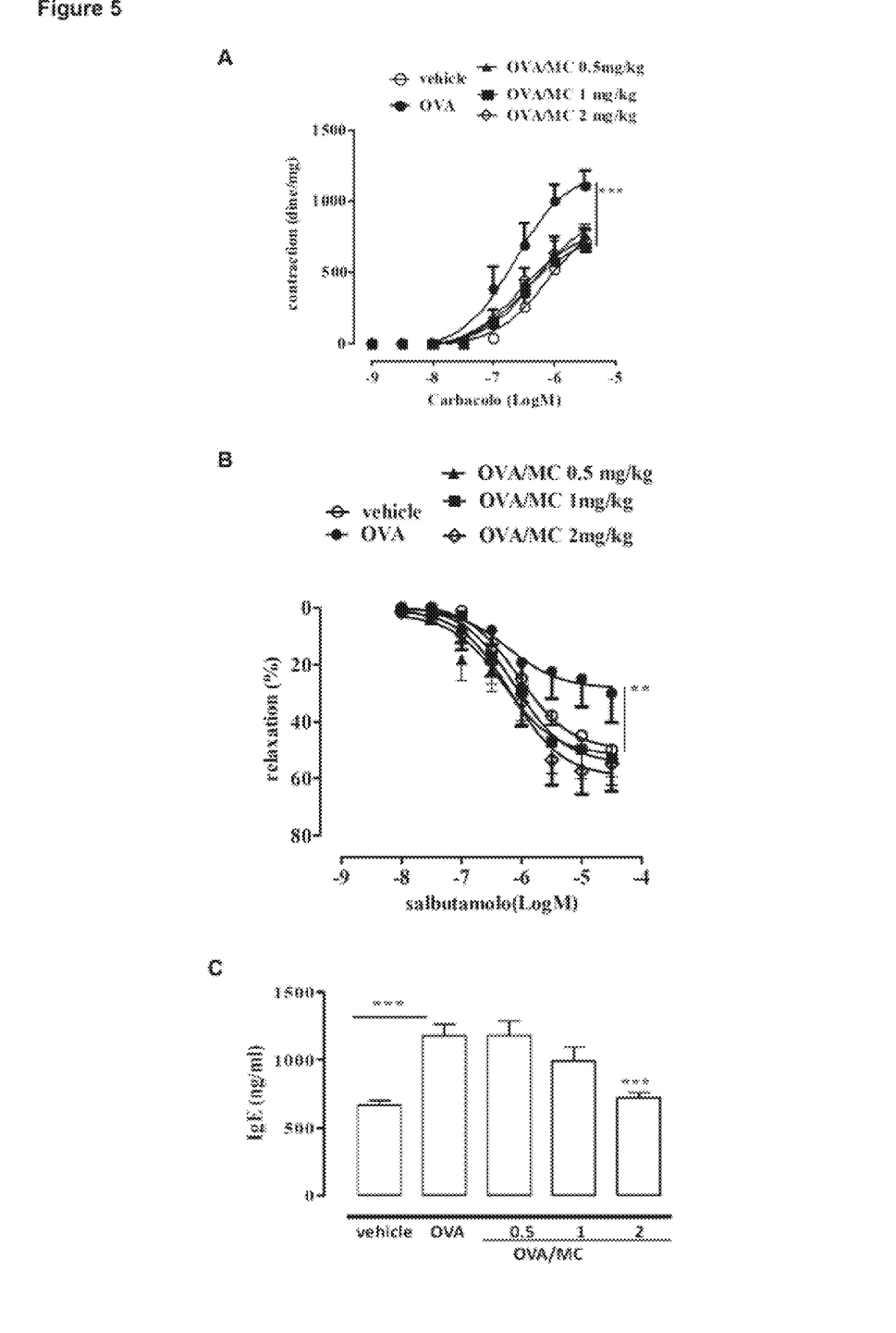
FIG. 5. Effects of montelukast desisobutyryl-ciclesonide ester (MC) on bronchial reactivity in mice with OVA-induced allergic asthma. (A) Bronchoconstriction was assessed following carbachol challenge; *p<0001 vs vehicle. (B) Relaxation was assessed following salbutamol challenge p<0.01 vs vehicle. (C) Plasma IgE measurements ***p<0.001 vs OVA.
Figure 6:
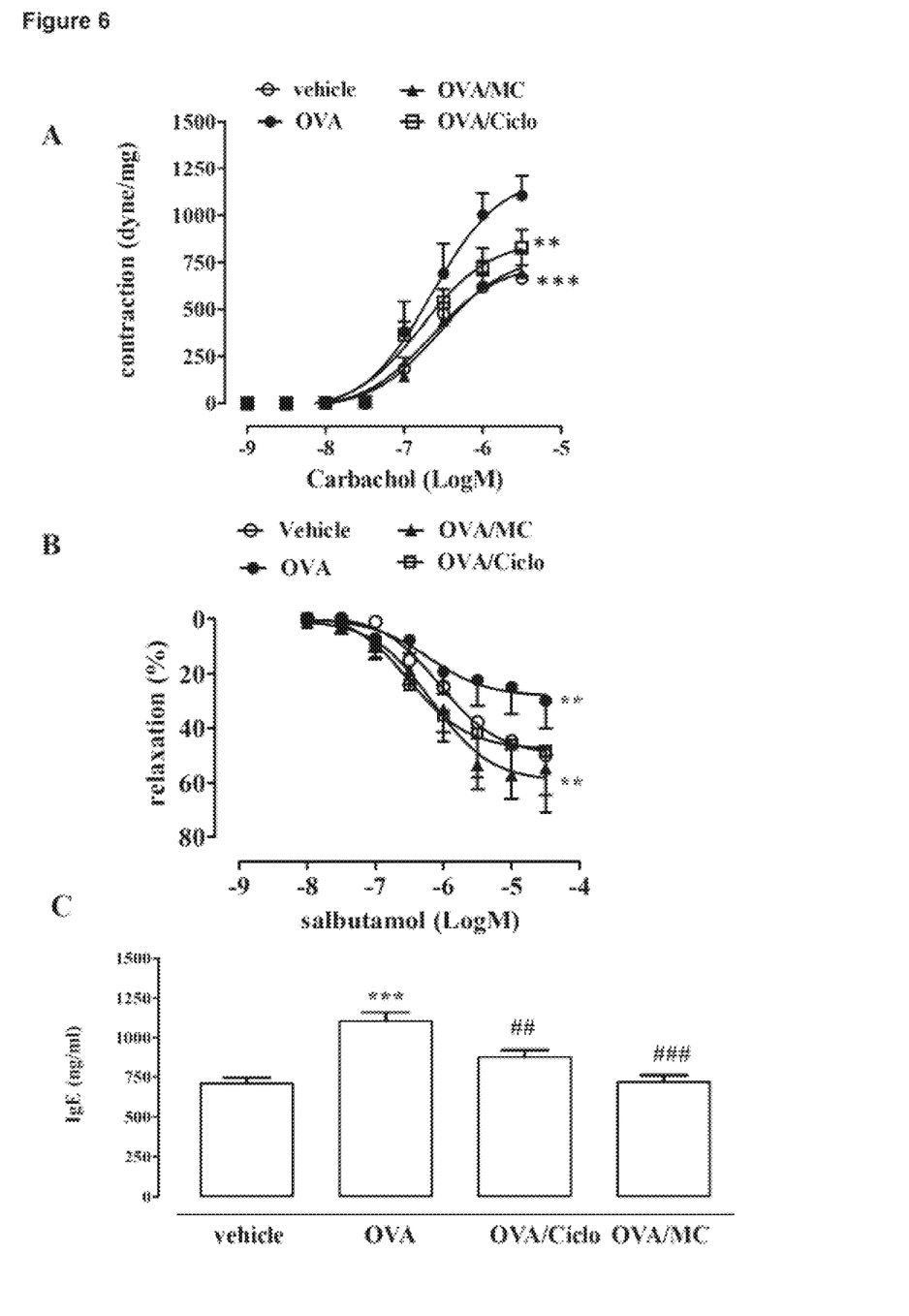
FIG. 6. Effects of montelukast desisobutyryl-ciclesonide ester (MC) and ciclesonide (Ciclo) on bronchial reactivity in mice with OVA-Induced allergic asthma. (A) Bronchoconstriction was assessed following carbachol challenge; *p<0001, p<0.01 vs OVA. (B) Relaxation was assessed following salbutamol challenge p<0.01 vs vehicle. (C) Plasma IgE measurements *p<0.001 vs vehicle; ##p<0.01, ###p<0.001 vs OVA.

OVA sensitization Induces at the bronchial level: i) an increase in the response to carbachol and ii) a reduced response to salbutamol (FIGS. 5A and 6B). Pharmacological treatment with montelukast desisobutyryl-ciclesonide ester (Formula V; MC) resulted in a good control of bronchial hyper-reactivity at all doses tested (FIG. 5A). Furthermore, the sensitization determines an inflammatory condition that causes a significant reduction in the response to beta-adrenergic agonists, which today represent the most effective drugs in the control of hyper-reactivity. Montelukast desisobutyryl-ciclesonide ester abrogated the increased response to carbachol, but rescued salbutamol ability to inducing bronchial relaxation at all doses tested (FIG. 5B). At the dose of 2 mg/Kg montelukast desisobutyryl-ciclesonide ester caused a further increase in salbutamol-induced relaxation when compared to vehicle. The efficacy of montelukast desisobutyryl-ciclesonide ester in the control of allergen-induced sensitization and in turn on asthma-like features was confirmed by IgE plasma dosage. Indeed, as shown in FIG. 6C, montelukast desisobutyryl-ciclesonide ester reduces allergen induced IgE increase in a dose-dependent manner.

In another series of experiments we compared the therapeutic efficacy of montelukast desisobutyryl-ciclesonide ester at the dose of 2 mg/kg to ciclesonide (Ciclo), 1 mg/kg; (FIG. 6) and montelukast (M) 1 mg/kg (FIG. 7).

Figure 7:
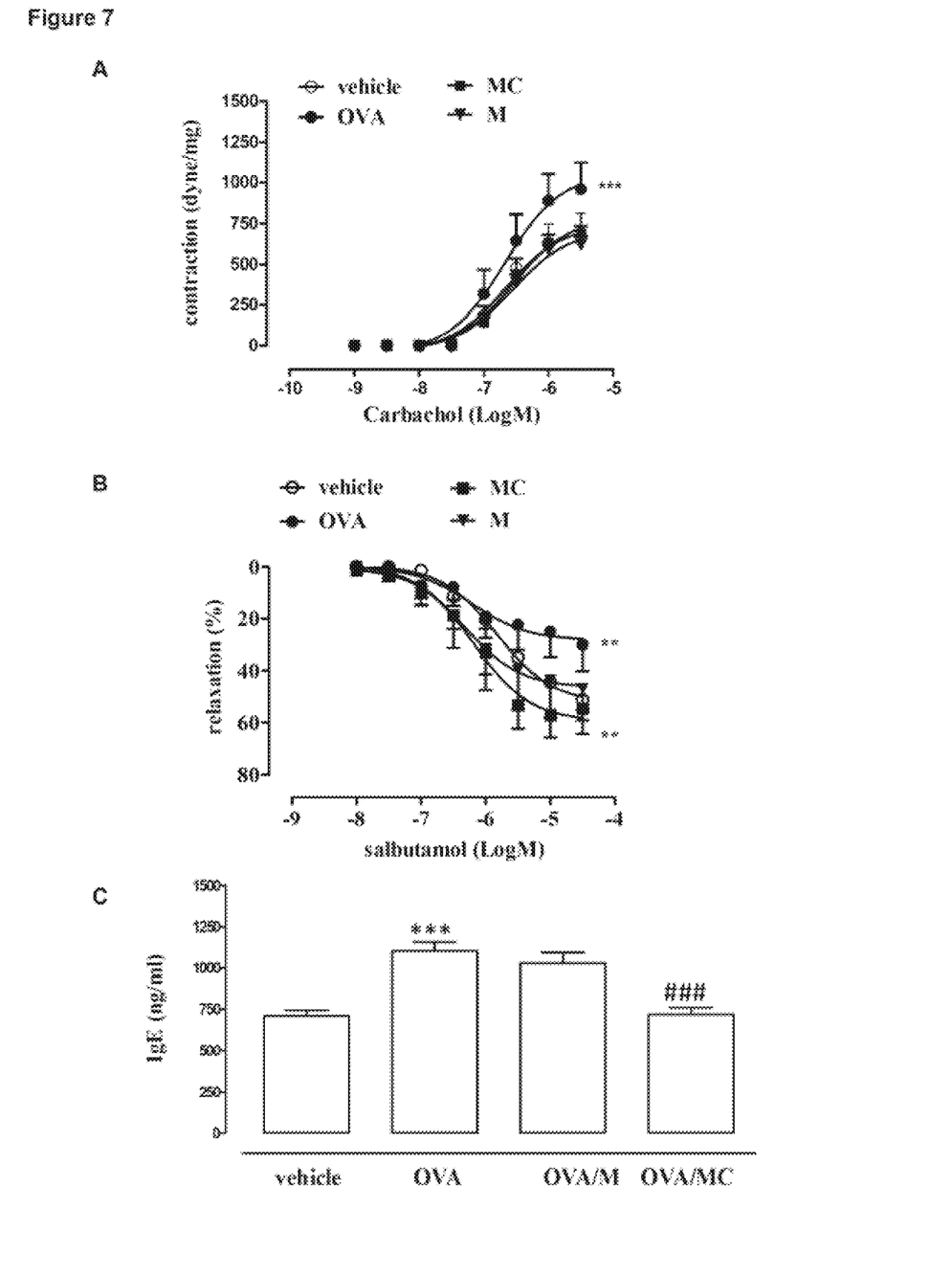
FIG. 7. Effects of montelukast desisobutyryl-ciclesonide ester (MC) and montelukast (M) on bronchial reactivity in mice with OVA-induced allergic asthma. (A) Bronchoconstriction was assessed following carbachol challenge; *p<0001 vs vehicle. (B) Relaxation was assessed following salbutamol challenge p<0.01 vs vehicle. (C) Plasma IgE measurements ***p<0.001 vs vehicle: ###p<0.001 vs OVA.

The results obtained confirmed the superiority of the montelukast desisobutyryl-ciclesonide ester in preserving the bronchial function; montelukast desisobutyryl-ciclesonide ester at equimolar doses with the parent drugs (FIGS. 6 and 7). Montelukast desisobutyryl-ciclesonide ester when compared to Ciclesonide showed a major efficacy in the control of the development of hyper-reactivity to carbachol induced by sensitization (FIG. 6A). In addition, montelukast desisobutyryl-ciclesonide ester displayed a significant major efficacy in preserving salbutamol induced bronchial relaxation when compared to ciclesonide (FIG. 6O). The pharmacological superiority of montelukast desisobutyryl-ciciesonide ester was confirmed by IgE plasma dosage, where ciclesonide significantly inhibited allergen induced IgE increase, but again montelukast desisobutyryl-ciclesonide ester showed an increased inhibitory effect (FIG. 6C).

Thus, montelukast desisobutyryl-ciciesonide ester is pharmacologically active following in vivo administration and mimics in vivo the additive pharmacological effect of ciclesonide and montelukast.

Treatment of sensitized mice with montelukast showed a significant inhibition of OVA-induced bronchial hyper-responsiveness (FIG. 7A). This effect is comparable to the effect obtained by montelukast desisobutyryl-ciclesonide ester confirming montelukast key role in modulating bronchial reactivity (FIG. 7A). In addition, we observed a significant effect of montelukast in preserving adrenergic relaxation induced by salbutamol. This effect was significantly enhanced by the montelukast desisobutyryl-ciclesonide ester (FIG. 7B). Since the reduction of adrenergic response relies on the inflammatory allergic reaction, it is plausible to attribute this additional effect to ciclesonide counterpart. This hypothesis is sustained by the changes in plasma IgE dosage (FIG. 7C). Indeed, montelukast did not affect IgE as compared to ciclesonide.

Protocol-2: Results

Figure 8:
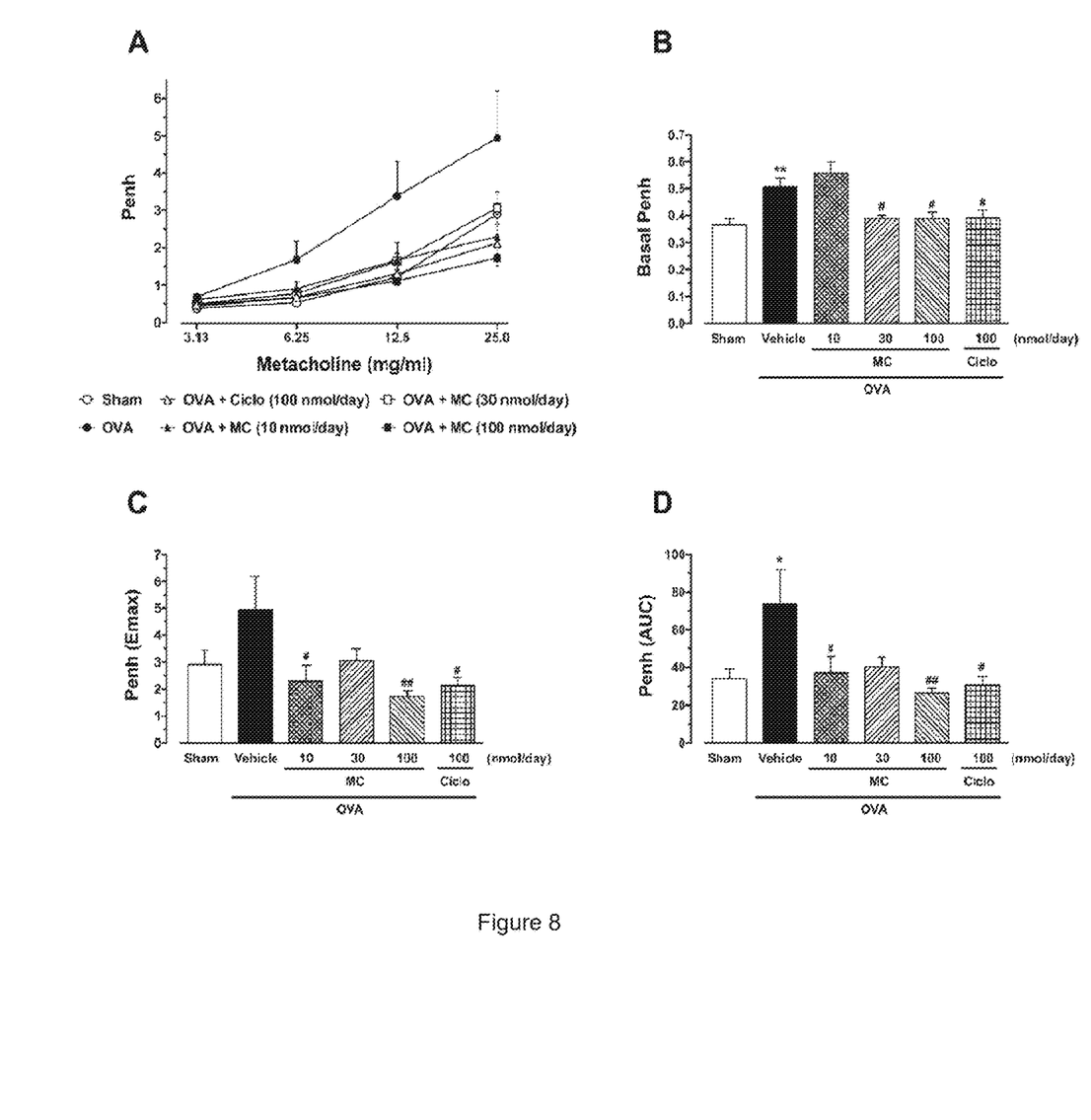
Figure 9:
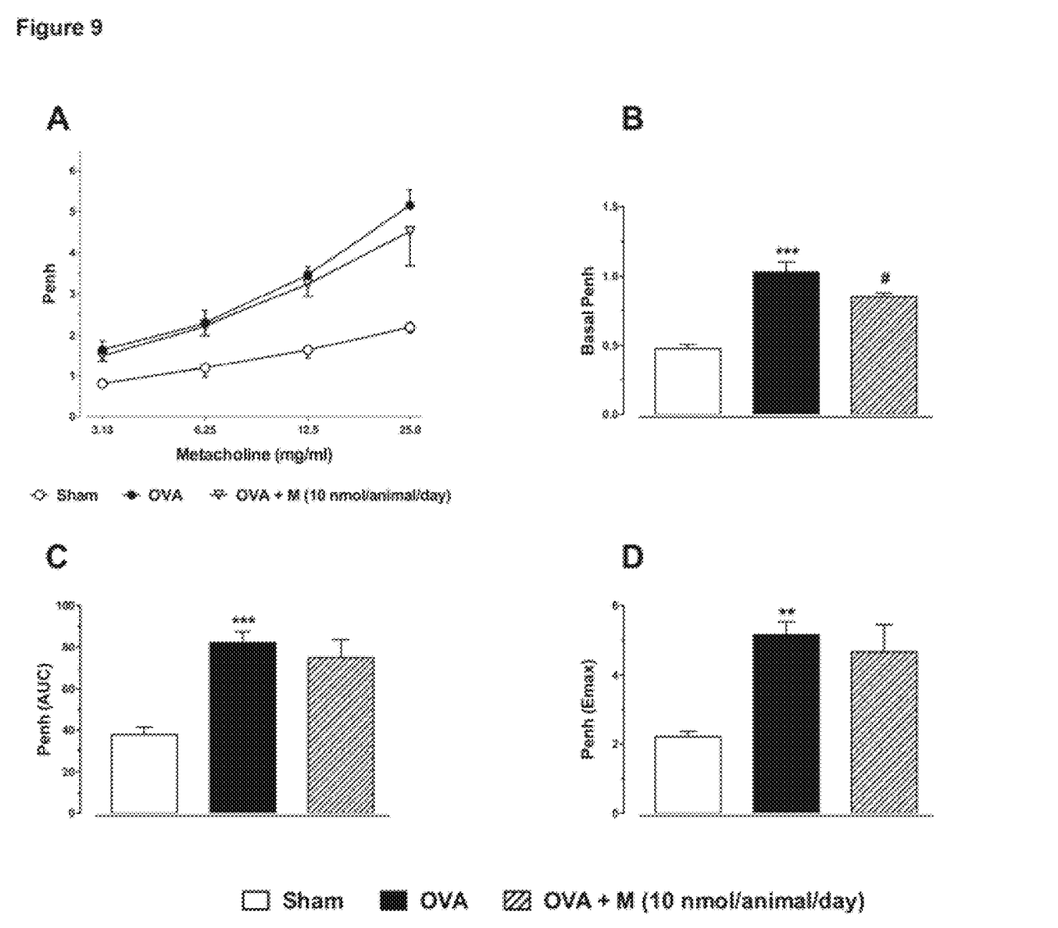
FIG. 9. Effects of montelukast (M) on Penh measurements in mice with OVA-induced allergic asthma. Bronchoconstriction was assessed by the enhanced pause response (Penh) measured after exposure of the unrestrained animals to inhaled saline solution (panel B) and increasing concentrations of inhalatory methacholine (MCh; panel A). Montelukast (at 10 nmol/animal) administered daily for 4 weeks, and 30 min before the OVA challenge (twice a week). Each data point represents mean±SEM for n=6 animals/group. Panel A: MCh dose vs. response curves; panel C: peak Penh responses (Emax); panel D: areas under the Penh vs. MCh dose curves (AUC). P<0.01 and *P<0.001 vs. Sham; #P<0.05 vs. untreated OVA group, as analyzed by one-way ANOVA followed by the Dunnett test.

OVA-induced allergy significantly increased airway responsiveness, as assessed by the Penh measurement under basal conditions (inhalation of PBS solution; FIGS. 8B and 9B). Increasing concentrations of methacholine inhalation resulted in a dose dependent-increase of Penh function. The OVA-induced allergic challenge significantly increased airway responsiveness (FIGS. 8A and 9A), as demonstrated by the increased maximal response (Emax: FIGS. 8C and 9C) and the area under the Penh-metacholine concentration curve (AUC; FIGS. 8D and 9D). Significant reduction of this response was observed in the allergic animals treated with either ciclesonide or montelukast desisobutyryl-ciclesonide ester at the tested doses (FIG. 8A-D). As shown in FIG. 9, montelukast (at 10 nmol/animal/day) significantly reduced the basal Penh measurement (FIG. 9B), but did not affect the parameters measured following methacholine challenge (FIG. 9C-D).

Figure 10:
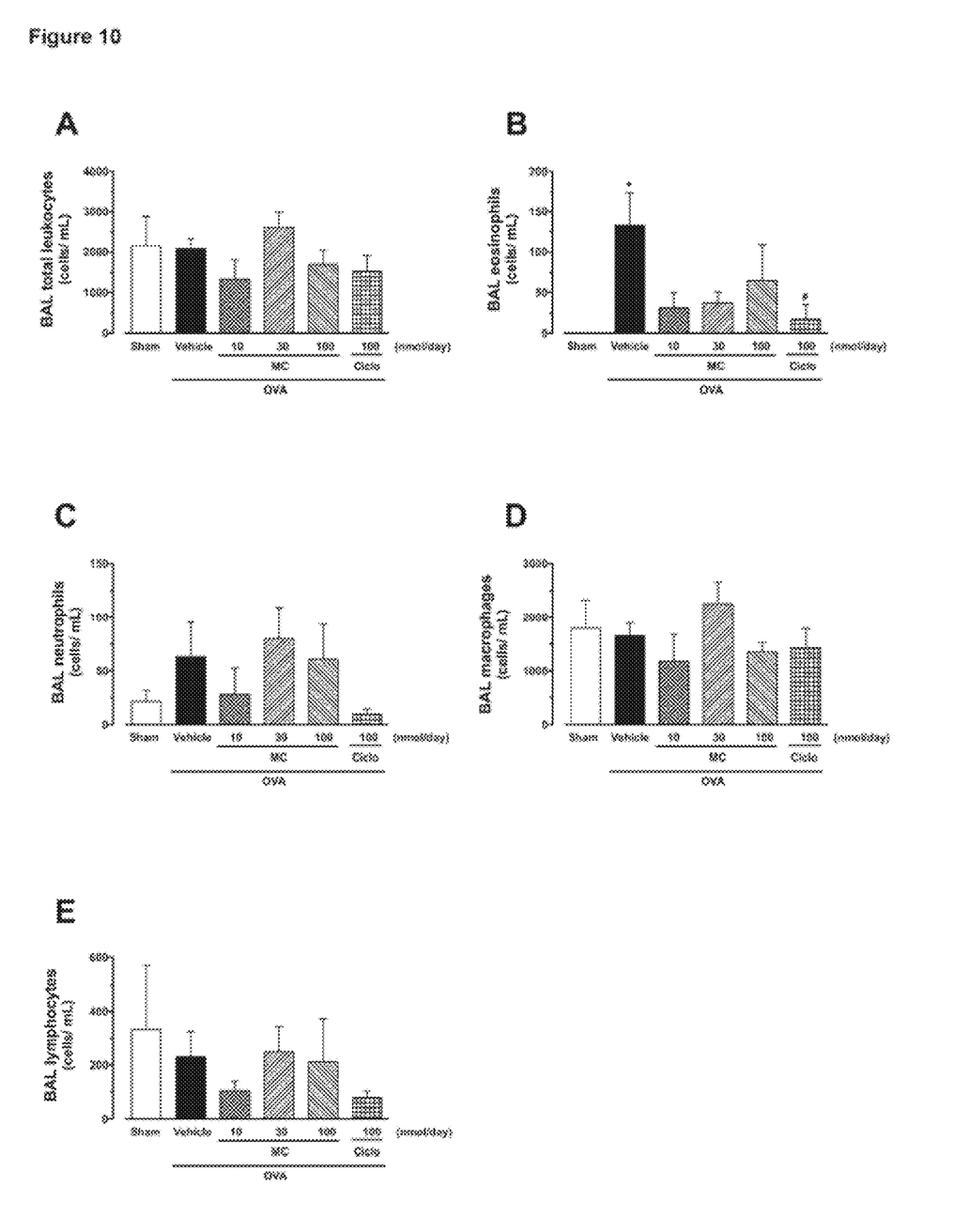
FIG. 10. Effects of Montelukast desisobutyryl-ciclesonide ester (MC) and ciclesonide (Ciclo) on total and differential leukocytes counts in DAL fluid harvested from mice with OVA4-induced allergic asthma. BAL fluids were harvested from untreated (sham) or OVA-induced allergic animals. Montelukast desisobutyryl-ciclesonide ester or ciclesonide were daily administered for 4 weeks, and 30 min before the OVA challenge (twice a week). Each bar represents mean±SEM for n=6 animals/group, except for Sham group (n=5). Panel A: Total BAL leukocytes; panel B: BAL eosinophils; panel C: BAL neutrophils; panel D: BAL macrophages; panel E: BAL lymphocytes. *P<0.05 vs. Sham; #P<0.05 vs. untreated OVA group, as analyzed by one-way ANOVA followed by the Dunnett test.
Figure 11:
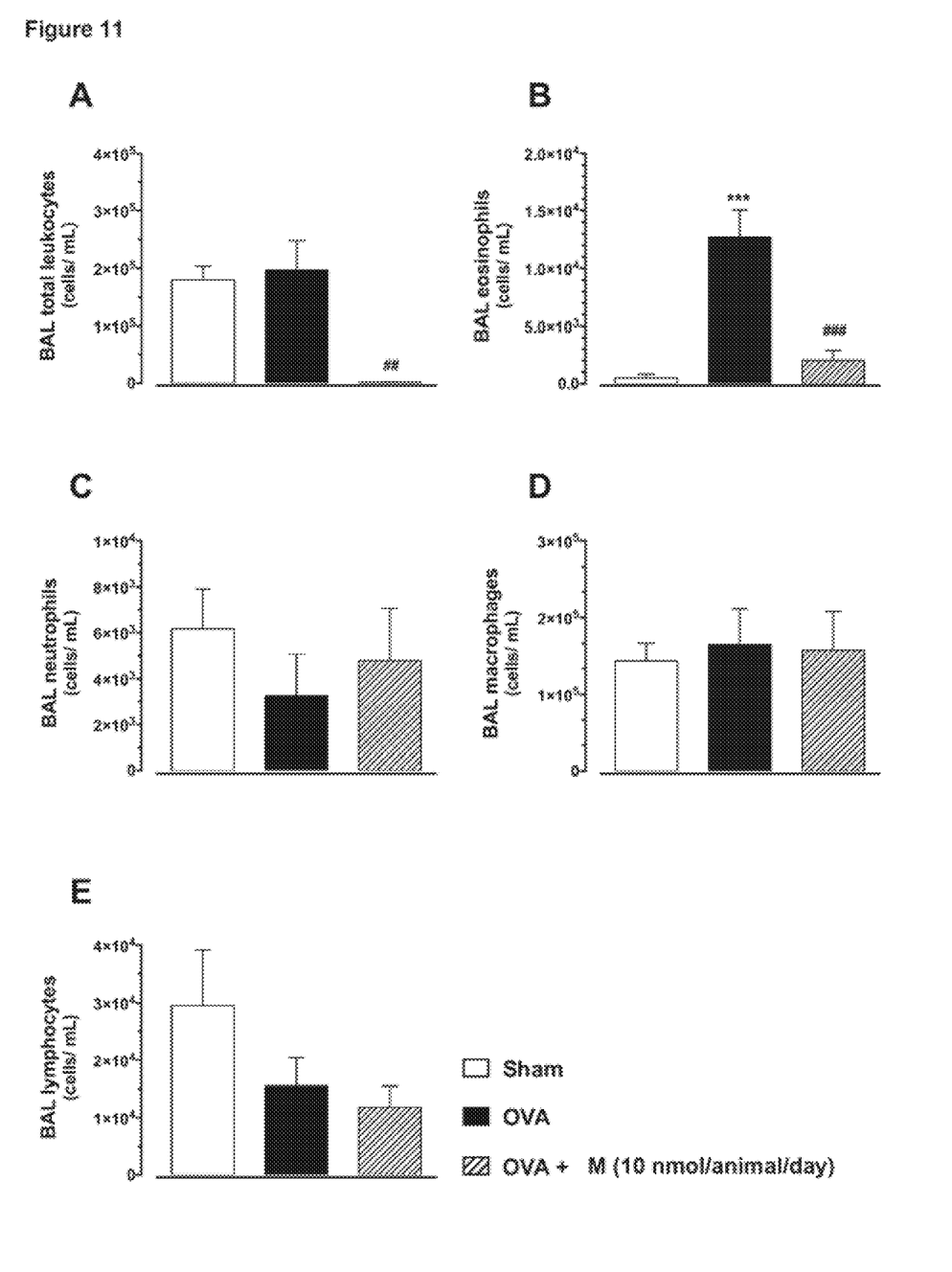
FIG. 11. Effects of Montelukast (M) on total and differential leukocytes counts in BAL fluid harvested from mice with OVA-induced allergic asthma. BAL fluids were collected from untreated (sham) or OVA-induced allergic animals. Montelukast was administered daily for 4 weeks, and 30 min before the OVA challenge (twice a week). Each bar represents mean±SEM for n=6 animals/group. Panel A: Total BAL leukocytes; panel 8: BAL eosinophils; panel C: BAL neutrophils; panel D: SAL macrophages; panel E: SAL lymphocytes, ***P<0.001 vs. Sham; ##P<0.01 and ###P<0.001 vs. untreated OVA group, as analysed by one-way ANOVA followed by the Dunnett test.

FIGS. 10 and 11 show that the number of total leukocytes in the collected BAL fluids were not significantly different among the different experimental groups (panel A). The same lack of effect was also observed for neutrophils (panel C), macrophages (panel D) or lymphocytes (panel E). Only BAL eosinophils were significantly augmented in the untreated OVA group ($P<0.05$). Ciclesonide treatment significantly reduced this increase ($P<0.05$), and despite the number of eosinophils were also lower in the montelukast desisobutyryl-ciclesonide ester-treated groups, these effects did not reach statistical significance.

No statistical differences among the experimental groups were observed in terms of either total or differential circulating leukocytes.

OVA-induced allergic asthma resulted in an increased airway responsiveness, as assessed by the Penh measurement. This effect was significantly reduced in the animals treated with either ciclesonide (at 100 nmol/day/animal) or montelukast desisobutyryl-ciclesonide ester (at doses of 10, 30 and 100 nmol/day/animal). Montelukast alone (at 10 nmol/day/animal) was only capable to slightly decrease the basal (non-challenged with methacholine) response, Thus, at this dose, montelukast has negligible direct effects on lung function.

As expected, this allergic condition was also characterized by an increased number of eosinophils recruited to the bronchoalveolar space, which was significantly reduced by the treatment with ciclesonide or montelukast. Despite not reaching statistical significance (due to the inter-individual variations), animals treated with montelukast desisobutyryl-ciclesonide ester (at the three tested doses) also exhibited lower number of eosinophils in the collected BAL fluids.

It is worthwhile mentioning that the doses used were calculated on the basis of previous published studies using the ovalbumin-induced asthma mouse model. Regarding ciclesonide, there are few studies published with mice. In a study were used 160 μg/day/animal equivalent to 296 nmol/day/animal (5.6) and in another study reporting were used 15 μg/day/animal, equivalent to 28 nmol/day/animal in a model of rhinitis (7). Considering that the ciclesonide doses used for treatment of asthmatic patients range from 160 to 640 μg/day, we concluded that in these animal studies the ciclesonide doses are too high and do not allow to rule out a significant systemic effect. For this reason, we decided to use lower dosed of ciclesonide i.e. 54.1 μg/day/animal equivalent to 100 nmol/day/animal. Accordingly the doses used to study the effect of montelukast desisobutyryl-ciclesonide ester were 100, 30 and 10 nmol/animal/day.

In the case of montelukast, the doses used in animal studies ranged from 1 mg/kg/day (equivalent to 1.7 μmol/kg/day) to 25 mg/kg/day (equivalent to 43 μmol/kg/day), although in these studies lung function was not always evaluated, and the studies were mainly focused on the inflammatory cell recruitment to the lungs (8-10). For the sake of comparisons, the montelukast desisobutyryl-ciclesonide ester doses used in the present study were approximately 0.35, 1.07 and 3.5 μmol/kg/day. Interestingly, during the second set of experiments aimed to test the effects of montelukast alone (at 10 nmol/animal/day equivalent to 0.35 μmol/kg/day), we observed significant inhibitory effects on eosinophil recruitment to the lungs Implying that montelukast could contribute, to the anti-inflammatory effects of displayed by the ciclesonide alone.

The presence of a positive synergism displayed by montelukast desisobutyryl-ciclesonide is supported by the finding that: i) at the lowest dose tested (10 nmol/animal/day) showed significant effects both in terms of respiratory function and inhibition of eosinophil recruitment to the lungs, which were comparable with those of ciclesonide alone at 100 nmol/animal/day ii) montelukast desisobutyryl-ciclesonide ester theoretically supplies 30 times less ciclesonide, and 6 to 120 times less montelukast than the effective doses reported in the literature.

All together this data demonstrates the efficacy in vivo of montelukast desisobutyryl-ciclesonide ester in modulating efficiently airway function. This effect was evident in both protocols where the ester of the present Invention was administered through two different administration routes intraperitoneal and intranasal at different doses. In addition, the ester of the present invention significantly reduces allergen-induced IgE raise, implying the ability to prevent exacerbation episodes in asthma management.

REFERENCES

[1]. Foster J M, Aucott L, van der Werf R H, van der Meijden M J, Schraa G. Postma D S, van der Molen T. Higher patient perceived side effects related to higher dailydoses of inhaled corticosteroids in the community: a cross-sectional analysis. Respir Med. 2006 August; 100(8): 1318-36
[2], Laforest L, El Hasnaoui A. Pribil C, Ritleng C, Osman L M, Schwalm M S, Le Jeunne P, Van Ganse E. Asthma patients' self-reported behaviours toward inhaled corticosteroids. Respir Med. 2009 September; 103(9):1366-75.
[3]. Derom E. Van De Velde V. Marissens S, Engelsttter R, Vincken W, Pauwels R. Effects of inhaled ciclesonide and fluticasone propionate on cortisol secretion and airway responsiveness to adenosine 5'monophosphate in asthmatic patients. Pulm Pharmacol Ther. 2005; 18(5):328-38.
[4]. dos Santos P R, Iskender I, Machuca T, Hwang D, dePerrot M. Liu M. Keshavjee S, Waddell T K, Cypel M. Modified in vivo lung perfusion allows for prolonged perfusion without acute lung Injury. J Thorac Cardiovasc Surg. 2014 February; 147(2):774-81: discussion 781-2.
[5]. Zuśka-Prot M, Maślanka T (2017), Inhaled glucocorticoid treatment prevents the response of CD8+ T cells in a mouse model of allergic asthma and causes their depletion outside the respiratory system. Int Immunopharmacol, 53: 63-72.
[6]. Zuśka-Prot M, Maślanka T (2017). Effect of inhaled and systemic glucocorticoid treatment on CD4+ regulatory and effector T cells in a mouse model of allergic asthma. Int Immunopharmacol, 45: 98-109.
[7], Kim Hs, Won S, Lee Ek, Chun Yh, Yoon Js, Kim Jt, Kim Hh (2017). Effect of Proparacaine in a Mouse Model of Allergic Rhinitis. Clin Exp Otorhinolaryngol, 10: 325-331.
[8]. Henderson Wr Jr. Tang Lo, Chu Sj, Tsao Sm, Chiang Gk, Jones F. Jonas M, Pae C. Wang H. Chi Ey (2002). A role for cysteinyl leukotrienes in airway remodeling in a mouse asthma model. Am J Respir Crit Care Med, 165: 108-16.
[9]. Eum Sy, Maghni K, Hamid Q, Campbell H, Eidelman Dh, Martin Jg (2003). Involvement of the cysteinyl-leukotrienes in allergen-induced airway eosinophilia and hyperresponsiveness in the mouse. Am J Respir Cell Mol Biol. 28: 25-32.
[10]. Wu Ay. Chik Sc, Chan Aw, Li Z, Tsang Kw, Li W (2003). Anti-inflammatory effects of high-dose montelukast in an animal model of acute asthma. Clin Exp Allergy, 33: 359-66.

The invention claimed is:
1. An ester of Montelukast with a corticosteroid selected from the group consisting of des-ciclesonide, triamcinolone, budesonide and flunisolide or a pharmaceutically acceptable salt, hydrate, or isomer thereof.
2. The ester according to claim 1, wherein the corticosteroid is des-ciclesonide.
3. The ester according to claim 1, which is a compound of Formula V:

FORMULA V or a pharmaceutically acceptable salt, hydrate, or isomer thereof.

4. A process for the preparation of the ester according to claim 1, comprising the steps of:
   i) dissolving or suspending Montelukast and a corticosteroid selected from the group consisting of des-ciclesonide, triamcinolone, budesonide and flunisolide in an organic solvent;
   ii) isolating the ester of Montelukast with the corticosteroid.

5. The process according to claim 4, wherein the organic solvent is selected from the group consisting of C1-C4 chlorinated hydrocarbons, C2-C4 nitriles, N,N-dimethylamides and mixtures thereof.

6. The process according to claim 5, wherein the organic solvent is selected from the group consisting of dichloromethane, chloroform, dichloroethane, acetonitrile, DMF, DMA and mixtures thereof.

7. The process according to claim 4, wherein the mmol/mL ratio between Montelukast and the organic solvent is from 0.05 mmol/mL to 0.1 mmol/mL.

8. The process according to claim 4, wherein the molar ratio between Montelukast and the corticosteroid is from 1 to 1.25.

9. The process according to claim 4, wherein the isolation step ii) is carried out by crystallization.

10. The process according to claim 9, wherein the isolation step ii) is carried out by crystallization from hexane, petroleum ether, diethyl ether or dichloromethane.

11. The process according to claim 4, wherein the corticosteroid is des-ciclesonide.

12. A pharmaceutical composition comprising the ester according to claim 1, in combination with at least one physiologically acceptable excipient.

13. The pharmaceutical composition according to claim 12, wherein the composition is in the form of aerosol, dry powder, solution or suspension.

14. The pharmaceutical composition according to claim 13, which is packaged for administration by inhalation or oral route.

15. A method for treating respiratory tract diseases, chronic obstructive pulmonary disease (COPD) and allergic rhinitis, in a subject in need thereof, comprising administration of an effective amount of the ester according to claim 2, alone or in combination with one or more physiologically acceptable excipients.

16. The method according to claim 15, wherein the respiratory tract disease is asthma.

* * * * *